(12) United States Patent
Ahn et al.

(10) Patent No.: US 12,102,464 B2
(45) Date of Patent: Oct. 1, 2024

(54) BONE AGE ESTIMATION METHOD AND APPARATUS

(71) Applicant: KOREA UNIVERSITY RESEARCH AND BUSINESS FOUNDATION, Seoul (KR)

(72) Inventors: Byung Duk Ahn, Seoul (KR); In Seok Song, Seoul (KR); Yoon-Ji Kim, Seoul (KR); Jae Gul Choo, Gyeonggi-do (KR); Jin Hee Kim, Seoul (KR); Tae Sung Kim, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 338 days.

(21) Appl. No.: 17/763,103

(22) PCT Filed: Dec. 15, 2020

(86) PCT No.: PCT/KR2020/018320
§ 371 (c)(1),
(2) Date: Mar. 23, 2022

(87) PCT Pub. No.: WO2021/149918
PCT Pub. Date: Jul. 29, 2021

(65) Prior Publication Data
US 2022/0386976 A1 Dec. 8, 2022

(30) Foreign Application Priority Data

Jan. 23, 2020 (KR) .................. 10-2020-0009524
Jun. 2, 2020 (KR) .................. 10-2020-0066130

(51) Int. Cl.
*A61B 6/50* (2024.01)
*A61B 6/00* (2024.01)
(Continued)

(52) U.S. Cl.
CPC .............. *A61B 6/505* (2013.01); *A61B 6/463* (2013.01); *A61B 6/469* (2013.01); *A61B 6/5217* (2013.01);
(Continued)

(58) Field of Classification Search
CPC ......... A61B 6/505; A61B 6/463; A61B 6/469; A61B 6/5217; A61B 6/54; G06T 7/0012;
(Continued)

(56) References Cited

U.S. PATENT DOCUMENTS

2003/0053673 A1* 3/2003 Dewaele ............... G06T 7/0012
382/209
2007/0078674 A1* 4/2007 Weinberg ........... G06Q 10/0637
705/7.36
(Continued)

FOREIGN PATENT DOCUMENTS

JP 2008541892 11/2008
KR 20140144645 12/2014
(Continued)

OTHER PUBLICATIONS

Arif et al, "Fully automatic cervical vertebrae segmentation framework for X-ray images" (published in Computer Methods of Programs in Biomedicine, vol. 157, pp. 95-111, Apr. 2018).*
(Continued)

*Primary Examiner* — Casey L Kretzer
(74) *Attorney, Agent, or Firm* — Hodgson Russ LLP

(57) ABSTRACT

Disclosed are a bone age estimation method and a bone age estimation apparatus. The bone age estimation method may comprise the steps of: extracting a region of interest including a cervical spine region from a lateral cephalometric radiographic image obtained by imaging a subject's cervical spine, by using a first deep learning model; extracting landmarks from the extracted region of interest by using a
(Continued)

second deep learning model; calculating a landmark numerical value on the basis of the extracted landmarks; and providing maturity information of a maturation stage of the cervical spine on the basis of the calculated landmark numerical value.

15 Claims, 5 Drawing Sheets

(51) Int. Cl.
    *A61B 6/46*     (2024.01)
    *G06T 7/00*     (2017.01)
    *G06T 7/64*     (2017.01)

(52) U.S. Cl.
    CPC .............. *A61B 6/54* (2013.01); *G06T 7/0012* (2013.01); *G06T 7/64* (2017.01); *G06T 2207/10116* (2013.01); *G06T 2207/20081* (2013.01); *G06T 2207/20101* (2013.01); *G06T 2207/30012* (2013.01)

(58) Field of Classification Search
    CPC .............. G06T 7/64; G06T 2207/10116; G06T 2207/20081; G06T 2207/20101; G06T 2207/30012
    See application file for complete search history.

(56) References Cited

U.S. PATENT DOCUMENTS

| | | | | |
|---|---|---|---|---|
| 2011/0320515 | A1* | 12/2011 | Mohammed | G16H 30/20 709/201 |
| 2016/0364837 | A1* | 12/2016 | Aoyama | G06T 11/60 |
| 2018/0232603 | A1* | 8/2018 | Shim | A61B 5/00 |
| 2019/0171914 | A1* | 6/2019 | Zlotnick | G06F 18/41 |

FOREIGN PATENT DOCUMENTS

| | | |
|---|---|---|
| KR | 20160028576 | 3/2016 |
| KR | 20160051355 | 5/2016 |
| KR | 20160099442 | 8/2016 |
| KR | 20170016778 | 2/2017 |
| KR | 101839784 | 3/2018 |
| KR | 101839789 | 3/2018 |
| KR | 20180045551 | 5/2018 |
| KR | 20190142234 | 12/2019 |
| KR | 20200005984 | 1/2020 |
| WO | 2012039467 | 3/2012 |

OTHER PUBLICATIONS

Baptista et al., "A semi-automated method for bone age assessment using cervical vertebral maturation," Angle Orthodontist, 2012, vol. 82, No. 4.

WIPO, International Search Report for PCT/KR2020/018320, Mar. 26, 2021.

* cited by examiner

BONE AGE ESTIMATION METHOD AND APPARATUS

CROSS-REFERENCE TO RELATED APPLICATIONS

This application is a U.S. national stage entry of International Application No. PCT/KR2020/018320, filed Dec. 14, 2020, which claims priority to Korean Application No. 10-2020-0009524, filed Jan. 23, 2020, and Korean Application No. 10-2020-0066130, filed Jun. 2, 2020, the entire disclosures of which are incorporated herein by reference

TECHNICAL FIELD

The following description relates to a bone age estimation technique.

BACKGROUND

In the field of orthodontics, deep learning based diagnostic assistance programs which mark anatomical landmarks limited to the upper jaw, the lower jaw, and skull and automatically perform orthodontic analysis thereby are currently released in the related art. However, the related art has a characteristic in that it is limited to diagnosis of orthodontics problems of the patient in the current state. Due to this characteristic, the related art has a limitation that it may not be applied to a technique of predicting a growing stage of the patient. Accordingly, there is a need for research to supplement the limitation of the related art.

SUMMARY

According to an aspect, a bone age estimation method may include extracting a region of interest including a cervical spine region from a lateral cephalometric radiographic image obtained by imaging a subject's cervical spine, by using a first deep learning model; extracting landmarks from the extracted region of interest by using a second deep learning model; calculating a landmark numerical value on the basis of the extracted landmarks; and providing maturity information of a maturation stage of the cervical spine on the basis of the calculated landmark numerical value.

The step of calculating a landmark numerical value may include: a step of calculating a landmark numerical value including at least one of a ratio of a height to a length of the cervical spine lower border, a ratio of a height to a length of the cervical spine lower border that draws a vertical line, and a concavity ratio of the cervical spine lower border, on the basis of the coordinates of the landmarks.

The step of extracting landmarks may include: a step of changing a coordinate of the extracted landmarks on the basis of the user input when a user input to change the extracted landmark is received.

The bone age estimation method according to the example embodiment may further include training the second deep learning model on the basis of the changed coordinate when the coordinate of the extracted landmark is changed by the user input.

The step of providing maturity information may include: a step of visually providing the maturity information of the cervical spine on the basis of at least one of a chronological age of the subject, a gender of the subject, age-specific standardization information for a concavity of the fourth cervical spine lower border corresponding to the gender of the subject, and a concavity ratio of the fourth cervical spine lower border of the subject.

In the step of providing maturity information, at least one of a graph corresponding to the standardization information, a graph corresponding to the concavity ratio of the fourth cervical spine lower border of the subject, and a graph corresponding to the chronological age of the subject may be provided to be overlaid.

The bone age estimation method according to the example embodiment may further include a step of adjusting a brightness of the region of interest and reversing left and right of the region of interest after extracting the region of interest.

The step of extracting landmarks may include: a step of providing a numerical value obtained by calculating a progress degree that the landmarks are extracted by a percentage, on the basis of a predetermined period.

The region of interest may include at least one of a second cervical spine, a third cervical spine, and a fourth cervical spine of the subject.

Each of the extracted landmarks is assigned with a tracking number on the basis of a position of each of the landmarks and the landmarks and the tracking numbers corresponding to the landmarks may be displayed in the region of interest.

It may be determined whether to display the extracted landmarks on the basis of a user input for selecting a landmark to be displayed.

The landmarks may be points obtained by anatomically measuring and marking at least one of the second cervical spine, the third cervical spine, and the fourth cervical spine of the subject.

According to another aspect, a bone age estimation apparatus which performs a bone age estimation method includes a memory and a processor, the memory stores instructions executable by the processor, and when the instructions are executed by the processor, the processor may control the bone age estimation apparatus to allow the bone age estimation apparatus to extract a region of interest including a cervical spine region from a lateral cephalometric radiographic image obtained by imaging a subject's cervical spine, by using a first deep learning model, extract landmarks from the extracted region of interest by using a second deep learning model, calculate a landmark numerical value on the basis of the extracted landmarks, and provide maturity information of a maturation stage of the cervical spine on the basis of the calculated landmark numerical value.

The processor may control the bone age estimation apparatus to allow the bone age estimation apparatus to calculate a landmark numerical value including at least one of a ratio of a height to a length of the cervical spine lower border, a ratio of a height to a length of the cervical spine lower border that draws a vertical line, and a concavity ratio of the cervical spine lower border, on the basis of the coordinates of the landmarks.

The processor may control the bone age estimation apparatus to allow the bone age estimation apparatus to change a coordinate of the extracted landmarks on the basis of the user input when a user input to change the extracted landmark is received.

The processor may control the bone age estimation apparatus to allow the bone age estimation apparatus to train the second deep learning model on the basis of the changed coordinate when the coordinate of the extracted landmark is changed by the user input.

The processor may control the bone age estimation apparatus to allow the bone age estimation apparatus to visually provide the maturity information of the cervical spine on the basis of at least one of a chronological age of the subject, a gender of the subject, age-specific standardization information for a concavity of the fourth cervical spine lower border corresponding to the gender of the subject, and a concavity ratio of the fourth cervical spine lower border of the subject.

The processor may control the bone age estimation apparatus to allow the bone age estimation apparatus to provide at least one of a graph corresponding to the standardization information, a graph corresponding to the concavity ratio of the fourth cervical spine lower border of the subject, and a graph corresponding to the chronological age of the subject to be overlaid.

The landmarks may be points obtained by anatomically measuring and marking at least one of the second cervical spine, the third cervical spine, and the fourth cervical spine of the subject.

According to the example embodiment, a deep learning based program which predicts a growth of a skeleton through a lateral cephalometric radiographic image may be provided.

According to the example embodiment, a cervical spine region is automatically cropped from the lateral cephalometric radiographic image and anatomical landmarks of the cervical spine are automatically marked.

According to the example embodiment, a bone age of the cervical spine may be analyzed on the basis of the anatomical landmarks of the cervical spine which are automatically marked.

According to the example embodiment, an average cervical spine evaluation index of growing patients in Korea is provided on a graph to intuitively present the degree of distribution of specific patients on the table.

According to the example embodiment, problems of the related art such as inconvenience of taking hand skeleton radiographic images, additional costs, and the increase in the amount of radiation exposed to the patients of children and adolescents caused to predict the growth of the children and adolescents may be solved.

According to the example embodiment, the landmarks are automatically marked to shorten an amount of labor and times required for a clinician to make a diagnosis.

According to the example embodiment, the landmark numerical values are provided on one screen to allow the user to intuitively and comprehensively check the diagnostic result.

According to the example embodiment, the growth of orthodontic patients may be predicted.

DETAILED DESCRIPTION

Figure 1:
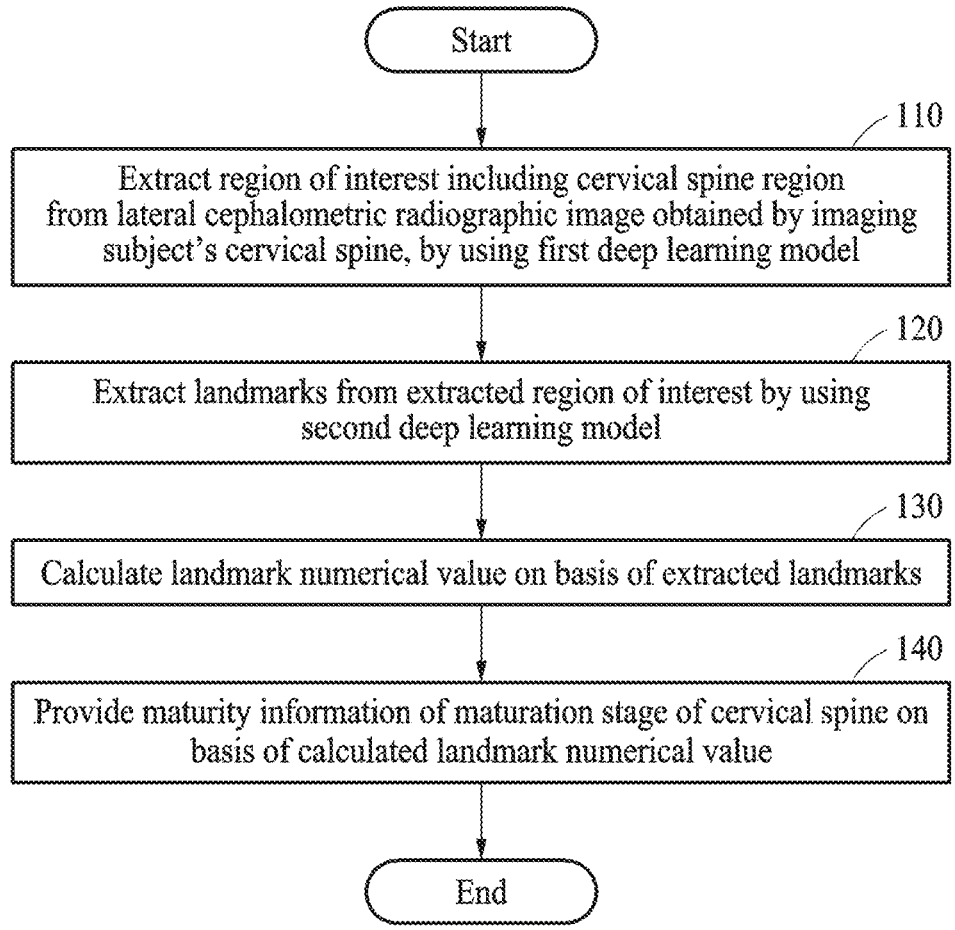
FIG. 1 is a flowchart for explaining a bone age estimation method according to an example embodiment.

Hereinafter, example embodiments will be described in detail with reference to the accompanying drawings. However, various changes may be applied to the example embodiments so that the scope of the application is not restricted or limited by the example embodiments. It should be understood that all changes, equivalents, or substitutes of example embodiments are included in the scope of the rights.

Terms used in the example embodiment are used only for illustrative purposes only, but should not be interpreted as an intention to limit the invention. A singular form may include a plural form if there is no clearly opposite meaning in the context. In the present specification, it should be understood that terminology "include" or "have" indicates that a feature, a number, a step, an operation, a component, a part or the combination thereof described in the specification is present, but do not exclude a possibility of presence or addition of one or more other features, numbers, steps, operations, components, parts or combinations, in advance.

If it is not contrarily defined, all terms used herein including technological or scientific terms have the same meaning as those generally understood by a person with ordinary skill in the art. Terms defined in generally used dictionary shall be construed that they have meanings matching those in the context of a related art, and shall not be construed in ideal or excessively formal meanings unless they are clearly defined in the present application.

In addition, in description with reference to accompanying drawings, the same components are denoted by the same reference numerals regardless of the reference numeral and a duplicated description thereof will be omitted. In description of an example embodiment, if it is determined that detailed description for a related art may unnecessarily blur the gist of the example embodiment, the detailed description will be omitted.

Further, in the description of the components of the example embodiment, a terminology such as a first, a second, A, B, (a), (b) may be used. However, such terminologies are used only to distinguish a component from another component but nature, a sequence or an order of the component is not limited by the terminologies. If it is described that a component is "connected" or "coupled" to another component, it is understood that the component is directly connected or coupled to the other component but another component may be "connected" or "coupled" between the components.

A component including a common function to a component included in any one example embodiment will be described with the same title in another example embodiment. If it is not contrarily defined, description of any one example embodiment may be applied to another example embodiment and a detailed description of overlapping parts will be omitted.

FIG. 1 is a flowchart for explaining a bone age estimating method according to an example embodiment.

A bone age estimation method described in the present specification may be disclosed by means of a program which assists the diagnosis of the radiographic image on the basis of artificial intelligence. The bone age estimation method may provide a method of dividing a skull and a facial bone of a lateral cephalometric radiographic image of the facial bone imaged for orthodontic diagnosis in the dentistry and automatically recognizing and marking anatomical landmarks such as a cervical spine. According to the bone age estimation method, a maturation stage of a cervical spine of a subject (or a patient) may be predicted using the recognized skull, facial bone, and landmarks. The bone age estimation method may be provided by a marking assistance program which analyzes an aspect of development of bones such as cervical spine and proposes a bone age required to grow the skeleton of the subject. The bone age estimation method may provide a method that helps to predict the growth of the orthodontic patient. The bone age estimation apparatus which is described in the present specification may be a computing device such as a desktop or a laptop or a portable terminal such as a tablet PC or a personal digital assistant (PDA).

Referring to FIG. 1, a bone age estimation apparatus may extract a region of interest including a cervical spine region from a lateral cephalometric radiographic image obtained by imaging a subject's cervical spine, by using a first deep learning model in step 100. In the example embodiment, the region of interest may include at least one of a second cervical spine, a third cervical spine, and a fourth cervical spine of the subject. The bone age estimation apparatus may display a lateral cephalometric radiographic image obtained by imaging a subject's cervical spine and the region of interest on one screen. After extracting the region of interest, the bone age estimation apparatus may adjust a brightness of the region of interest and reverse the left and right of the region of interest.

The bone age estimation apparatus may extract landmarks from the extracted region of interest by using a second deep learning model in step 120. Here, the landmarks may be points obtained by anatomically measuring and marking at least one of the second cervical spine, the third cervical spine, and the fourth cervical spine of the subject. The bone age estimation apparatus may extract thirteen landmarks corresponding to a lower border edge of the second cervical spine, an upper border edge and a lower border edge of the third cervical spine, and an upper border edge and a lower border edge of the fourth cervical spine from the region of interest using the second deep learning model. According to the example embodiment, the bone age estimation apparatus may provide a function of confirming that the landmarks are not completely extracted so as not to move to another image. That is, the bone age estimation apparatus may provide a function of moving to another image after extracting all thirteen landmarks. The bone age estimation apparatus may adjust sizes of the landmarks. A tracking number is assigned to each of extracted landmarks on the basis of the positions of the landmarks and the landmarks and the tracking numbers of the landmarks may be displayed in the region of interest. According to the example embodiment, it is determined whether to display the extracted landmarks on the basis of a user input to select a landmark to be displayed. That is, a user (or a medical specialist) may directly select landmarks to be displayed in the region of interest. For example, the user checks a checkbox to select a landmark to be displayed and undoes the checkbox to select a landmark which is not to be displayed.

When the bone age estimation apparatus receives a user input to change the extracted landmarks, the bone age estimation apparatus may change a coordinate of the extracted landmarks on the basis of the user input. That is, the user may modify the positions of the landmarks with respect to the landmarks extracted by the bone age estimation apparatus as intended by the user. When the coordinates of the extracted landmarks are changed by the user input, the bone age estimation apparatus may train the second deep learning model on the basis of the changed coordinate.

The bone age estimation apparatus may provide a numerical value obtained by calculating a degree to which the extraction of the landmarks is performed by a percentage, on the basis of a predetermined period, while extracting the landmarks. For example, the bone age estimation apparatus visually represents a progress that the extraction of the landmarks is completed by a percentage.

In step 130, the bone age estimation apparatus may calculate a landmark numerical value on the basis of the extracted landmark. The bone age estimation apparatus may calculate a landmark numerical value including at least one of a ratio of a height to a length of the cervical spine lower border, a ratio of a height to a length of the cervical spine lower border that draws a vertical line, and a concavity ratio of the cervical spine lower border, on the basis of the coordinates of the landmarks. The bone age estimation apparatus may calculate a ratio of a height to the length of the cervical spine lower border and a ratio of a height to the length of the cervical spine lower border which draws a vertical line, for the third cervical spine and the fourth cervical spine, and calculate a concavity ratio of the lower borders for the second cervical spine, the third cervical spine, and the fourth cervical spine.

During the process of calculating the ratio of the height to the length of the cervical spine lower border, a length of the lower border indicates a length of a line connecting front and rear peaks of the lower border and the height indicates an average value of two lengths between the lower border and the upper border.

During the process of calculating the ratio of the height to the length of the cervical spine lower border which draws a vertical line, a length of the lower border indicates a length of a line connecting front and rear peaks of the lower border and the height may indicate an average value of two straight distances between the lower border and the upper border.

The concavity ratio of the lower border may be a ratio of c to w when c is calculated by a straight distance to the deepest point of the lower border from a line connecting the front and rear peaks of the lower border and the length of the lower border is calculated by a length w of a line connecting the front and rear peaks of the lower border.

The bone age estimation apparatus may provide maturity information of a maturation stage of the cervical spine on the basis of the calculated landmark numerical value calculated in step 140. According to the example embodiment, the bone age estimation apparatus may visually provide the maturity information to the user.

The bone age estimation apparatus may visually provide the maturity information of the cervical spine on the basis of at least one of a chronological age of the subject, a gender of the subject, age-specific standardization information for a concavity of the fourth cervical spine lower border corresponding to the gender of the subject, and a concavity ratio of the fourth cervical spine lower border of the subject. Here, the chronological age may be calculated by dividing one year into four quarters.

The bone age estimation apparatus may provide at least one of a graph corresponding to the standardization information, a graph corresponding to the concavity ratio of the fourth cervical spine lower border of the subject, and a graph corresponding to the chronological age of the subject to be overlaid. The bone age estimation apparatus may represent the standardization information for the concavity ratio of the fourth cervical spine lower border on the graph, represent the chronological age of the subject with a vertical line thereon and represent the concavity ratio of the fourth cervical spine lower border with a horizontal line. The user may confirm a standard growth for the age of the subject through the graph on which three information is overlaid.

Figure 2A:
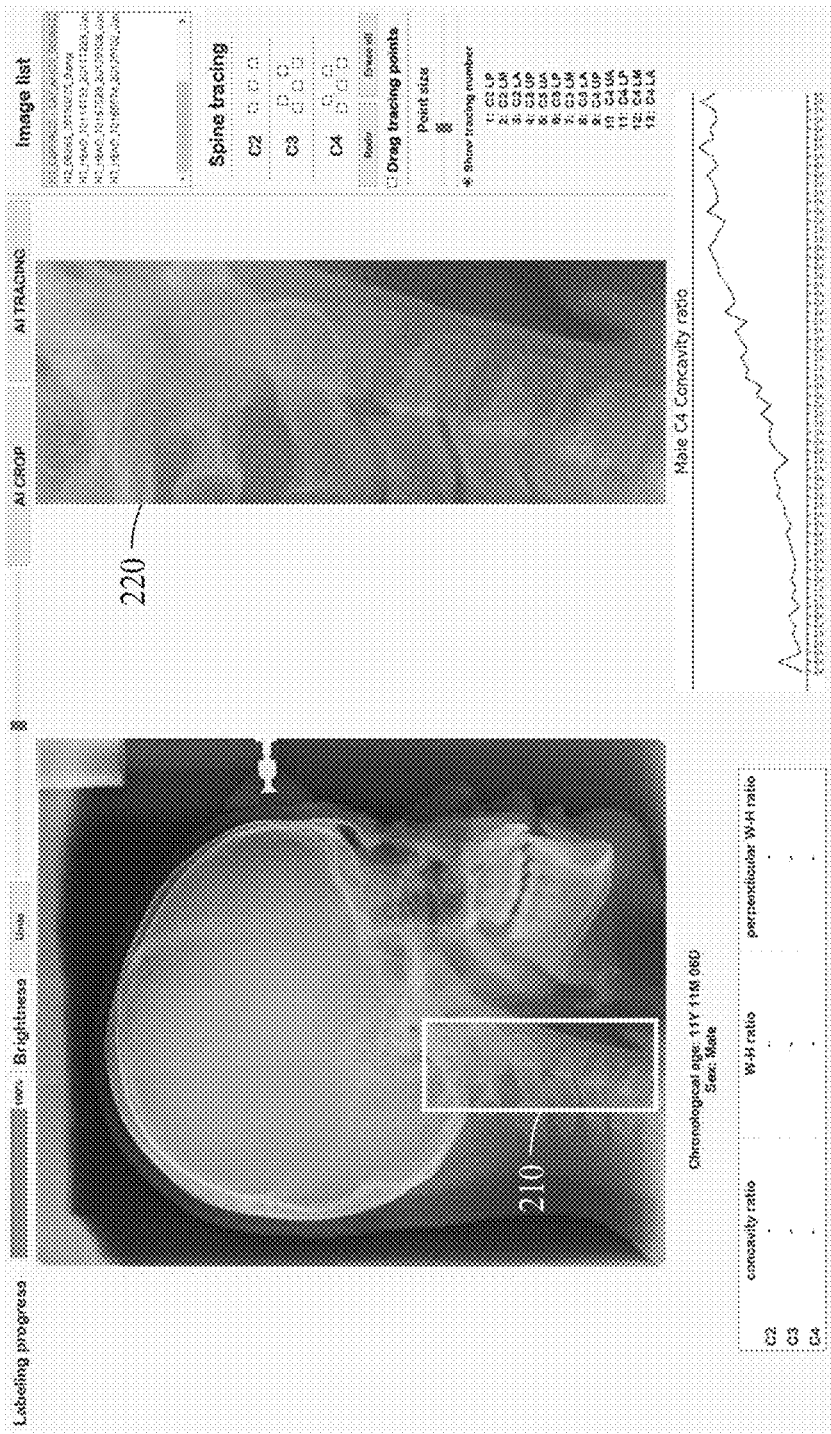
FIGS. 2A to 2C are views illustrating examples of an interface in which a bone age estimation method according to an example embodiment is performed.
Figure 2B:
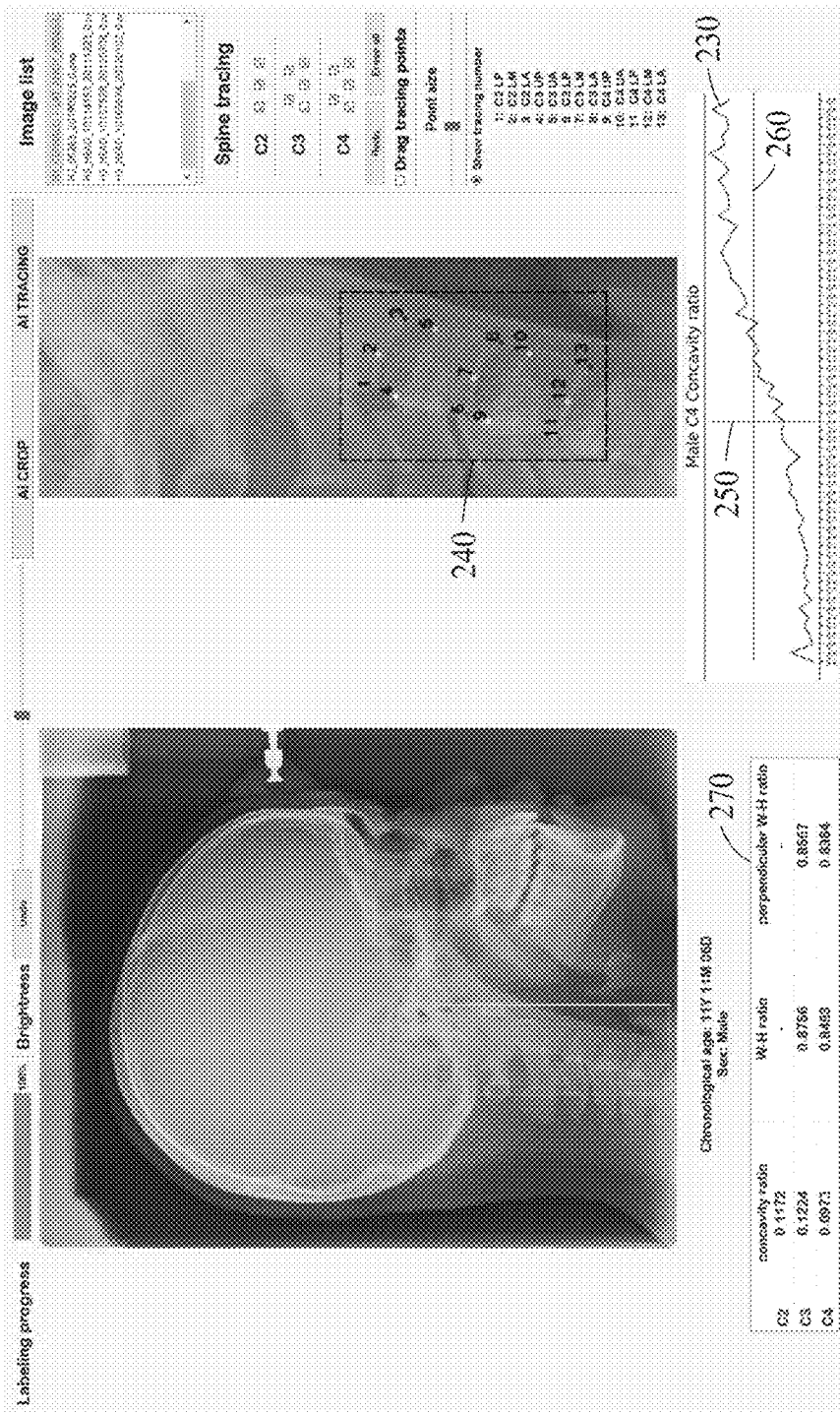
Figure 2C:
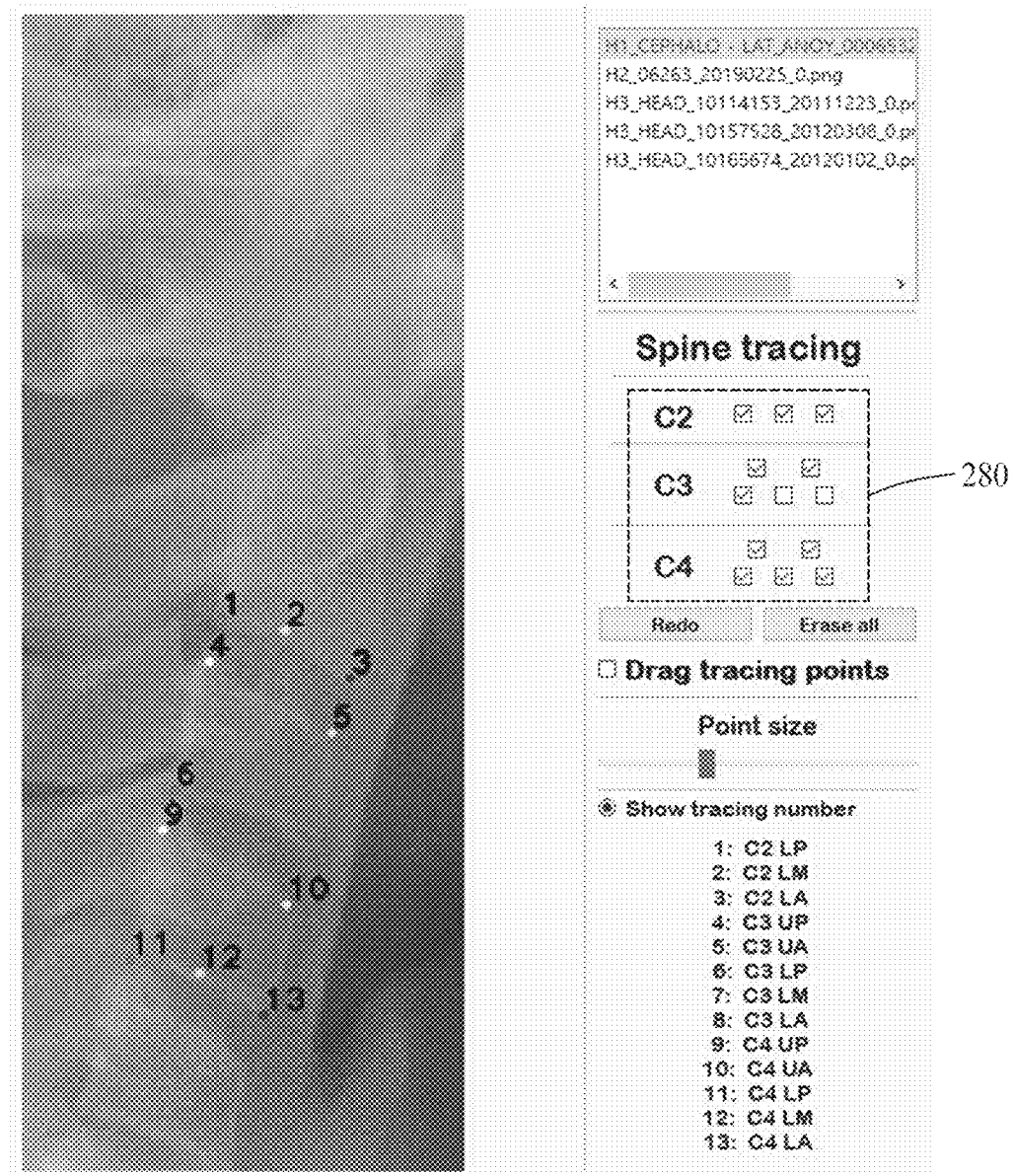

FIGS. 2A to 2C are views illustrating examples of an interface in which a bone age estimation method according to an example embodiment is performed.

The bone age estimation apparatus may provide a cephalometric image and a cropped region of interest 220 including a cervical spine region 210 of the patient in an interface of FIG. 2A. A region 210 cropped from the cephalometric image may be represented by a bounding box. The region 210 represented by the bounding box and the cropped region of interest 220 which is displayed on the right may be the same image.

The landmarks 240 extracted from an interface of FIG. 2B may be displayed on the region of interest. The interface of FIG. 2B may include landmark numeric values 270 calculated on the basis of coordinate information of the landmarks. Further, the interface of FIG. 2B may include a graph 230 representing a concavity ratio of the fourth cervical spine corresponding to the gender of the patient, a vertical graph 250 representing a chronological age of the patient, and a horizontal graph 260 representing a concavity ratio of the fourth cervical spine lower border. The bone age estimation apparatus provides three graphs 230, 250, and 260 to be overlaid to allow the user to intuitively confirm the maturity information of the cervical spine of the patient. The user or the patient may confirm a maturity relative to the standard growth level corresponding to the age of the patient.

An interface which is provided by the bone age estimation apparatus to perform a bone age estimation method may visually provide a numerical value obtained by calculating a degree that the extraction of the landmarks is completed by a percentage. Further, the interface may provide a region in which a user input to adjust a brightness of the image in which the region of interest is cropped may be received.

The bone age estimation apparatus assigns a tracking number on the basis of a position of each of the landmarks to be displayed through an interface of FIG. 2C. According to the example embodiment, C2 LP corresponding to a tracking number 1 denotes a left landmark of a lower border of the second cervical spine, C2 LM corresponding to a tracking number 2 denotes a middle landmark of the lower border of the second cervical spine, and C2 LA corresponding to a tracking number 3 denotes a right landmark of the lower border of the second cervical spine. C3 UP corresponding to a tracking number 4 denotes a left landmark of an upper border of the third cervical spine, C3 UA corresponding to a tracking number 5 denotes a right landmark of the upper border of the third cervical spine, C3 LP corresponding to a tracking number 6 denotes a left landmark of a lower border of the third cervical spine, C3 LM corresponding to a tracking number 7 denotes a middle landmark of the lower border of the third cervical spine, and C3 LA corresponding to a tracking number 8 denotes a right landmark of the lower border of the third cervical spine. C4 UP corresponding to a tracking number 9 denotes a left landmark of an upper border of the fourth cervical spine, C4 UA corresponding to a tracking number 10 denotes a right landmark of the upper border of the fourth cervical spine, C4 LP corresponding to a tracking number 11 denotes a left landmark of a lower border of the fourth cervical spine, C4 LM corresponding to a tracking number 12 denotes a middle landmark of the lower border of the fourth cervical spine, and C4 LA corresponding to a tracking number 13 denotes a right landmark of the lower border of the fourth cervical spine. In the reference numeral 280, the user checks or undoes a check box for each landmark to determine whether to display the landmarks. Referring to FIG. 2C, the user undoes the check boxes corresponding to the tracking number 7 and the tracking number 8 so as not to display a seventh landmark and an eighth landmark. The user may move the positions of the displayed landmarks at the user's discretion. Further, the user may also adjust the sizes of the displayed landmarks. According to the example embodiment, colors of the landmarks to be displayed may be determined on the basis of the position. For example, landmarks corresponding to the left of the lower border are displayed with red, landmarks corresponding to the middle of the lower border are displayed with green, landmarks corresponding to the right of the lower border are displayed with blue, landmarks corresponding to the left of the upper border are displayed with yellow, and landmarks corresponding to the right of the upper border are displayed with sky blue.

Figure 3:
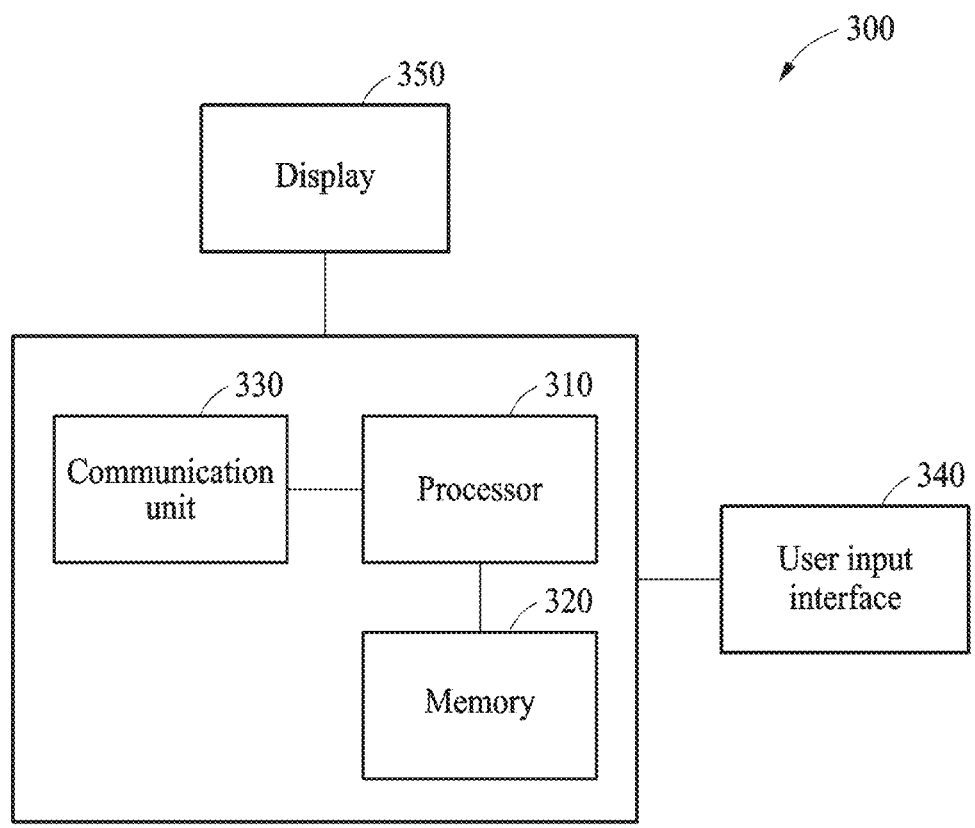
FIG. 3 is a view illustrating a bone age estimation apparatus according to an example embodiment.

FIG. 3 is a view illustrating a bone age estimation apparatus according to another example embodiment.

Referring to FIG. 3, a bone age estimation apparatus 300 corresponds to the bone age estimation apparatus described in the present specification. The bone age estimation apparatus 300 may include a processor 310, a memory 320, and a communication unit 330. Further, the bone age estimation apparatus 300 may further include a user input interface 340 and a display 350.

The memory 320 is connected to the processor 310 and stores instructions executable by the processor 310, data to be operated by the processor 310, or data processed by the processor 310. The memory 320 may include non-transitory computer-readable media, such as high-speed random access memories and/or non-volatile computer-readable storage media (for example, one or more disk storage devices, flash memory devices, or other non-volatile solid state memory devices).

The communication unit 330 provides an interface to communicate with an external device. For example, the communication unit 330 may receive a lateral cephalometric radiographic image from the external device.

The display 350 may output an example of a screen that the bone age estimation apparatus 300 executes an artificial intelligence based radiographic image diagnosis assistance program.

Further, the user input interface 340 may receive a user input to change extracted landmarks input by the user and a user input to select a landmark to be displayed.

The processor 310 may control the bone age estimation apparatus 300 to allow the bone age estimation apparatus 300 to perform one or more operations related to an operation of the bone age estimation apparatus 300.

For example, the processor 310 may control the bone age estimation apparatus 300 to allow the bone age estimation apparatus 300 to extract a region of interest including a cervical spine region from a lateral cephalometric radiographic image obtained by imaging subject's cervical spine by using a first deep learning model and extract landmarks from the extracted region of interest by using a second deep learning model.

The processor 310 may control the bone age estimation apparatus 300 to allow the bone age estimation apparatus 300 to calculate a landmark numerical value on the basis of the extracted landmark. The processor 310 may control the bone age estimation apparatus 300 to allow the bone age estimation apparatus 300 to calculate a landmark numerical value including at least one of a ratio of a height to a length of the cervical spine lower border, a ratio of a height to a length of the cervical spine lower border that draws a vertical line, and a ratio of a concavity of the cervical spine lower border, on the basis of the coordinates of the landmarks. When the bone age estimation apparatus 300 receives the user input to change the extracted landmarks, the processor 310 may control the bone age estimation apparatus 300 to change the coordinate of the extracted landmark on the basis of the user input. When the coordinate of the extracted landmark is changed by the user input, the processor 310 may control the bone age estimation apparatus 300 to train the second deep learning model on the basis of the changed coordinate.

The bone age estimation apparatus 300 may be controlled to provide maturity information of a maturation stage of the cervical spine on the basis of the calculated landmark numerical value. The processor 310 may control the bone age estimation apparatus 300 to allow the bone age estimation apparatus 300 to visually provide the maturity information of the cervical spine on the basis of at least one of a chronological age of the subject, a gender of the subject, age-specific standardization information for a concavity of the fourth cervical spine lower border corresponding to the gender of the subject, and a concavity ratio of the fourth cervical spine lower border of the subject. The processor 310 may control the bone age estimation apparatus 300 to allow the bone age estimation apparatus 300 to provide at least one of a graph corresponding to standardization information, a graph corresponding to a concavity ratio of a fourth cervical spine lower border of the subject, and a graph corresponding to a chronological age of the subject to be overlaid.

The method according to the example embodiment may be implemented as a program command which may be executed by various computers to be recorded in a computer readable medium. The computer readable medium may include solely a program command, a data file, and a data structure or a combination thereof. The program instruction recorded in the medium may be specifically designed or constructed for the example embodiment or known to those skilled in the art of a computer software to be used. Examples of the computer readable recording medium include magnetic media such as a hard disk, a floppy disk, or a magnetic tape, optical media such as a CD-ROM or a DVD, magneto-optical media such as a floptical disk, and a hardware device which is specifically configured to store and execute the program command such as a ROM, a RAM, and a flash memory. Examples of the program command include not only a machine language code which is created by a compiler but also a high level language code which may be executed by a computer using an interpreter. The hardware device may operate as one or more software modules in order to perform the operation of the example embodiment and vice versa.

The software may include a computer program, a code, an instruction, or a combination of one or more of them and configure the processing device to be operated as desired or independently or collectively command the processing device. The software and/or data may be permanently or temporarily embodied in an arbitrary type of machine, component, physical device, virtual equipment, computer storage medium, or device, or signal wave to be transmitted to be interpreted by a processing device or provide command or data to the processing device. The software may be distributed on a computer system connected through a network to be stored or executed in a distributed manner. The software and data may be stored in one or more computer readable recording media.

As described above, although example embodiments have been described by limited drawings, those skilled in the art may apply various technical modifications and changes based on the above description. For example, even when the above-described techniques are performed by different order from the described method and/or components such as systems, structures, devices, or circuits described above are coupled or combined in a different manner from the described method or replaced or substituted with other components or equivalents, the appropriate results can be achieved.

Therefore, other implements, other embodiments, and equivalents to the claims are within the scope of the following claims.

The invention claimed is:

1. A bone age estimation method, comprising the steps of:
 extracting a region of interest including a cervical spine region from a lateral cephalometric radiographic image obtained by imaging a subject's cervical spine, by using a first deep learning model;
 extracting landmarks from the extracted region of interest by using a second deep learning model;
 displaying landmarks as points in the region of interest on the basis of a user input selecting landmarks to be displayed and landmarks to not be displayed from the extracted landmarks;
 calculating a landmark numerical value on the basis of the displayed landmarks; and
 providing maturity information of a maturation stage of the cervical spine on the basis of the calculated landmark numerical value,
 wherein the step of providing maturity information includes:
  a step of visually providing the maturity information of the cervical spine on the basis of a gender of the subject, age-specific standardization information for a concavity of a fourth cervical spine lower border corresponding to the gender of the subject, and a concavity ratio of the fourth cervical spine lower border of the subject, and
  a step of providing a graph corresponding to the age-specific standardization information and a graph corresponding to the concavity ratio of the fourth cervical spine lower border of the subject to be overlaid.

2. The bone age estimation method of claim 1, wherein the step of calculating a landmark numerical value includes:
 a step of calculating a landmark numerical value including at least one of a ratio of a height to a length of the cervical spine lower border, a ratio of a height to a length of the cervical spine lower border that draws a vertical line, and a concavity ratio of the cervical spine lower border, on the basis of the coordinates of the landmarks.

3. The bone age estimation method of claim 1, wherein the step of extracting landmarks includes:
 a step of changing a coordinate of the extracted landmarks on the basis of the user input when a user input to change the extracted landmark is received.

4. The bone age estimation method of claim 3, further comprising:
 a step of training the second deep learning model on the basis of the changed coordinate when the coordinate of the extracted landmark is changed by the user input.

5. The bone age estimation method of claim 1, further comprising:
 a step of adjusting a brightness of the region of interest and reversing left and right of the region of interest after extracting the region of interest.

6. The bone age estimation method of claim 1, wherein the step of extracting landmarks includes:
 a step of providing a numerical value obtained by calculating a progress degree that the landmarks are extracted by a percentage, on the basis of a predetermined period.

7. The bone age estimation method of claim 1, wherein the region of interest includes at least one of a second cervical spine, a third cervical spine, and a fourth cervical spine of the subject.

8. The bone age estimation method of claim 7, wherein the landmarks are points obtained by anatomically measuring and marking at least one of the second cervical spine, the third cervical spine, and the fourth cervical spine of the subject.

9. The bone age estimation method of claim 1, wherein each of the extracted landmarks is assigned with a tracking number on the basis of a position of each of the landmarks, and the step of displaying landmarks further includes displaying tracking numbers corresponding to the displayed landmarks in the region of interest.

10. A non-transitory computer readable storage medium storing instructions that are operable with a processor to execute the method of claim 1.

11. A bone age estimation apparatus which performs a bone age estimation method, the apparatus comprising:
   a memory; and
   a processor;
   wherein the memory stores instructions executable by the processor that when executed by the processor, the processor controls the bone age estimation apparatus to allow the bone age estimation apparatus to extract a region of interest including a cervical spine region from a lateral cephalometric radiographic image obtained by imaging a subject's cervical spine, by using a first deep learning model, extract landmarks from the extracted region of interest by using a second deep learning model, display landmarks as points in the region of interest on the basis of a user input selecting landmarks to be displayed and landmarks to not be displayed from the extracted landmarks, calculate a landmark numerical value on the basis of the displayed landmarks, and provide maturity information of a maturation stage of the cervical spine on the basis of the calculated landmark numerical value,
   wherein the processor controls the bone age estimation apparatus to allow the bone age estimation apparatus to visually provide the maturity information of the cervical spine on the basis of a gender of the subject, age-specific standardization information for a concavity of a fourth cervical spine lower border corresponding to the gender of the subject, and a concavity ratio of the fourth cervical spine lower border of the subject,
   wherein the processor controls the bone age estimation apparatus to allow the bone age estimation apparatus to provide a graph corresponding to the age-specific standardization information and a graph corresponding to the concavity ratio of the fourth cervical spine lower border of the subject to be overlaid.

12. The bone age estimation apparatus of claim 11, wherein the processor controls the bone age estimation apparatus to allow the bone age estimation apparatus to calculate a landmark numerical value including at least one of a ratio of a height to a length of the cervical spine lower border, a ratio of a height to a length of the cervical spine lower border that draws a vertical line, and a concavity ratio of the cervical spine lower border, on the basis of the coordinates of the landmarks.

13. The bone age estimation apparatus of claim 11, wherein the processor controls the bone age estimation apparatus to allow the bone age estimation apparatus to change a coordinate of the extracted landmarks on the basis of the user input when a user input to change the extracted landmark is received.

14. The bone age estimation apparatus of claim 13, wherein the processor controls the bone age estimation apparatus to allow the bone age estimation apparatus to train the second deep learning model on the basis of the changed coordinate when the coordinate of the extracted landmark is changed by the user input.

15. The bone age estimation apparatus of claim 11, wherein the landmarks are points obtained by anatomically measuring and marking at least one of a second cervical spine, a third cervical spine, and a fourth cervical spine of the subject.

* * * * *